United States Patent
Mount

(10) Patent No.: US 12,343,460 B2
(45) Date of Patent: Jul. 1, 2025

(54) DEVICE FOR REDUCING AIRBORNE CONTAMINANTS

(71) Applicant: Randy A. Mount, Dayton, OH (US)

(72) Inventor: Randy A. Mount, Dayton, OH (US)

( * ) Notice: Subject to any disclaimer, the term of this patent is extended or adjusted under 35 U.S.C. 154(b) by 995 days.

(21) Appl. No.: 17/373,135

(22) Filed: Jul. 12, 2021

(65) Prior Publication Data

US 2022/0008608 A1 Jan. 13, 2022

Related U.S. Application Data

(60) Provisional application No. 63/051,061, filed on Jul. 13, 2020.

(51) Int. Cl.
*A61L 9/20* (2006.01)
*B01J 19/12* (2006.01)
*B01J 35/39* (2024.01)

(52) U.S. Cl.
CPC .............. *A61L 9/205* (2013.01); *B01J 19/123* (2013.01); *B01J 35/39* (2024.01); *A61L 2209/12* (2013.01); *B01J 2219/0892* (2013.01); *B01J 2219/32296* (2013.01)

(58) Field of Classification Search
CPC ... A61L 9/205; A61L 2/10; A61L 2/14; A61L 9/20; A61L 9/22; B01D 53/88; B01D 2255/802; B01D 2257/91; B01D 2258/06; B01D 2259/4508; B01J 19/123; B01J 2219/0873; B01J 2219/0892; B01J 2219/32296; B01J 35/00; H01T 23/00
See application file for complete search history.

(56) References Cited

U.S. PATENT DOCUMENTS

| | | | |
|---|---|---|---|
| 2,628,083 A * | 2/1953 | Rense | F24F 3/12 55/467 |
| 7,063,820 B2 * | 6/2006 | Goswami | A61L 2/02 422/186 |
| 8,585,979 B2 | 11/2013 | Tupman | |
| 8,585,980 B2 | 11/2013 | Tupman et al. | |
| 9,387,271 B2 | 7/2016 | Warren et al. | |
| 9,457,122 B2 | 10/2016 | Warren et al. | |
| 2007/0227362 A1 * | 10/2007 | Parker | B01D 46/0028 96/224 |
| 2014/0050610 A1 | 2/2014 | Tupman | |
| 2014/0050611 A1 | 2/2014 | Warren et al. | |
| 2015/0093293 A1 * | 4/2015 | Settu | B01D 39/2055 422/122 |
| 2017/0028093 A1 | 2/2017 | Tupman | |
| 2017/0274112 A1 | 9/2017 | Warren et al. | |
| 2018/0333512 A1 | 11/2018 | Tupman | |
| 2019/0030203 A1 | 1/2019 | Warren et al. | |
| 2021/0038755 A1 * | 2/2021 | Eide | B01D 53/885 |

* cited by examiner

*Primary Examiner* — Jennifer Wecker
*Assistant Examiner* — Brady C Pilsbury
(74) *Attorney, Agent, or Firm* — Thomas E. Lees, LLC

(57) ABSTRACT

A photocatalytic system for reducing airborne contaminants using an ultraviolet (UV) emitter and photocatalytic cells, the system comprises a housing comprising a front side having an opening therethrough, and a rear side opposite the front side, the rear side also having an opening therethrough. A first photocatalytic cell is located in the housing adjacent to the front side. Likewise, a second photocatalytic cell located in the housing adjacent to the rear side. A unitary removable structure slidably positionable within the housing between the first photocatalytic cell and the second photocatalytic cell.

18 Claims, 17 Drawing Sheets

DEVICE FOR REDUCING AIRBORNE CONTAMINANTS

CROSS REFERENCE TO RELATED APPLICATIONS

This application claims the benefit of U.S. Provisional Patent Application Ser. No. 63/051,061, filed Jul. 13, 2020, entitled "DEVICE FOR REDUCING AIRBORNE CONTAMINANTS", the disclosure of which is hereby incorporated by reference.

FIELD OF THE DISCLOSURE

The present disclosure relates generally to reducing airborne contaminants and, more particularly, to reducing airborne contaminants using ultraviolet (UV) energy.

DESCRIPTION OF RELATED ART

Ultraviolet (UV) light is a form of electromagnetic radiation with wavelength shorter than that of visible light, but with a wavelength longer than X-rays. UV light is known to interact with organic molecules. More particularly, deoxyribonucleic acid (DNA), ribonucleic acid (RNA), and proteins can absorb deep UV light, e.g., in the range of 200 nanometers (nm) to 300 nm, which can lead to rupture of a cell, disruption of DNA replication, and other molecular damage. As such, UV light is sometimes used to disinfect surfaces that might contain bacteria, mold, virus, etc.

SUMMARY

The present disclosure is directed to photocatalytic systems for reducing airborne contaminants using an ultraviolet (UV) emitter and photocatalytic cells.

In some embodiments, a photocatalytic system is provided for reducing airborne contaminants using an ultraviolet (UV) emitter and photocatalytic cells. The system comprises a housing having a front side having an opening therethrough, and a rear side opposite the front side, the rear side also having an opening therethrough. A first photocatalytic cell may be located in the housing adjacent to the front side. Likewise, a second photocatalytic cell may be located in the housing adjacent to the rear side. Still further, an embodiment may comprise both the first photocatalytic cell adjacent to the front side and the second photocatalytic cell adjacent to the rear side. A unitary removable structure is slidably positionable within the housing between the front side and the rear side.

In other embodiments, the system comprises a unitary removable structure comprising a first reflective portion, a second reflective portion, and a connective structure that mechanically connects the first reflective portion to the second reflective portion. The first reflective portion, the second reflective portion, and the connective structure are thus seamlessly integrated into the unitary removable structure.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE EMBODIMENTS

Figure 1A:
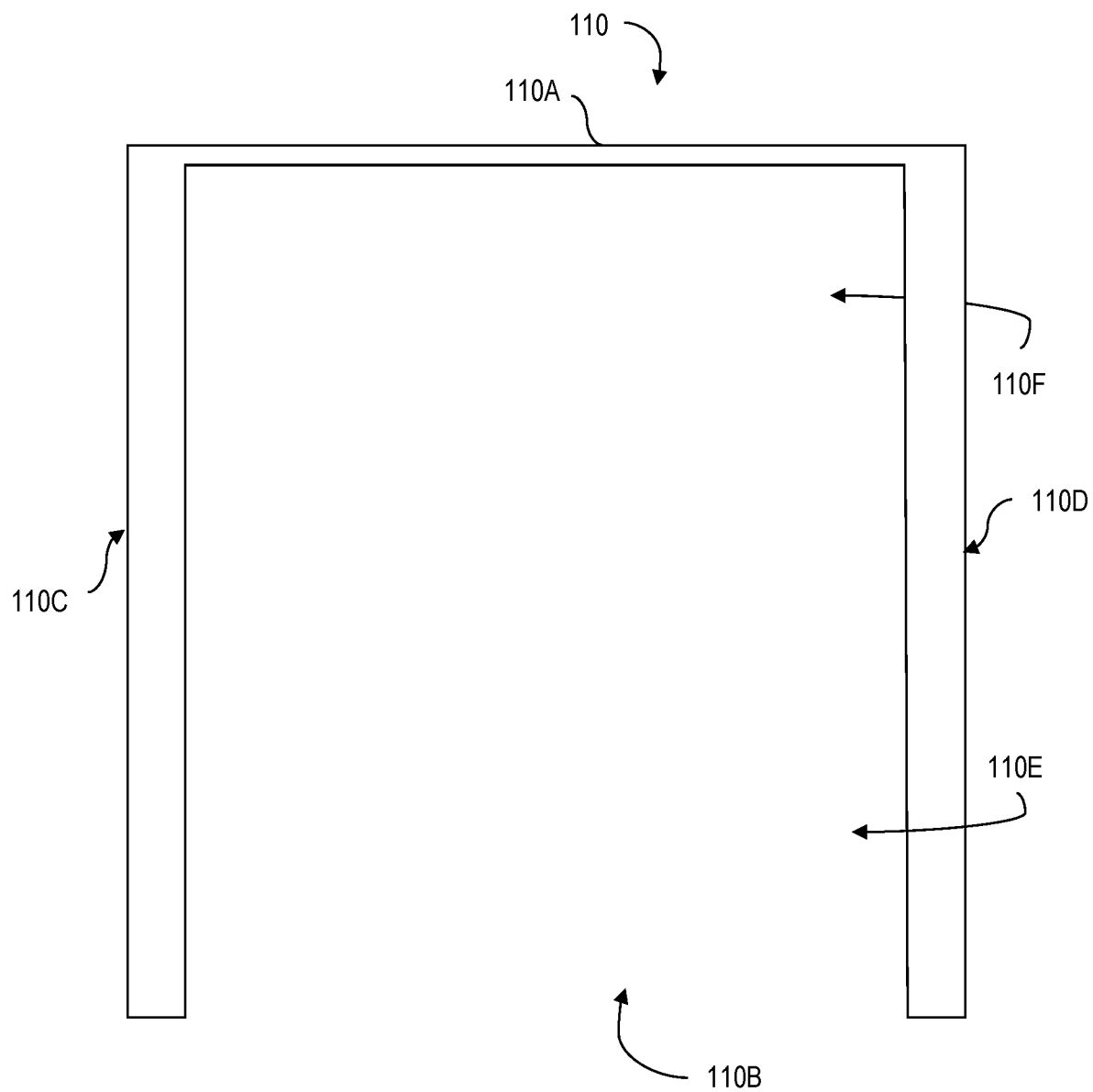
FIG. 1A is a diagram illustrating a housing component of a photocatalytic system for reducing airborne contaminants.

In the presence of ultraviolet (UV) energy, photocatalytic cells produce cluster ions or ionized clouds that reduce airborne contaminants, such as bacteria, mold, or virus. As air passes through the photocatalytic cells, UV energy that strikes the photocatalytic cells results in a catalytic reaction that produces ionized molecules within the airflow. The ionized molecules neutralize some or all of the contaminants that are present in the air.

The effectiveness of photocatalytic systems depends on the concentration of ionized molecules. The concentration of ionized molecules is, in turn, dependent on both: (a) the amount of photocatalytic material on the photocatalytic cells (e.g., titanium dioxide coated on honeycomb structured cells); and, also (b) how much UV strikes the photocatalytic material. In other words, merely having more photocatalytic material (e.g., titanium dioxide) is insufficient if the photocatalytic material is not exposed to the UV energy.

To mitigate losses in efficiency, several embodiments are disclosed, which provide for greater UV exposure to the photocatalytic materials. Specifically, some embodiments include a unitary removable reflector that is positioned within the photocatalytic system. The unitary removable reflector permits greater exposure of UV energy to the photocatalytic cells, thereby improving efficiency. Furthermore, by using a unitary removable structure (rather than multiple separate reflectors), the disclosed systems and processes allow for more streamlined assembly of UV-based photocatalytic systems. Still further, by providing the unitary removable structure in different configurations, described more fully below, the system can be readily configured and reconfigured, based upon the application, environment, and need. In some embodiments, the unitary removable structure can be retrofitted into pre-existing systems. The use of a unitary, removable structure thus allows tuning of a system, even on site, by selecting a particular unitary removable structure configuration.

Having provided a broad technical solution to a technical problem, reference is now made in detail to the description of the embodiments as illustrated in the drawings. While several embodiments are described in connection with these drawings, there is no intent to limit the disclosure to the embodiment or embodiments disclosed herein. On the contrary, the intent is to cover all alternatives, modifications, and equivalents.

Figure 1B:
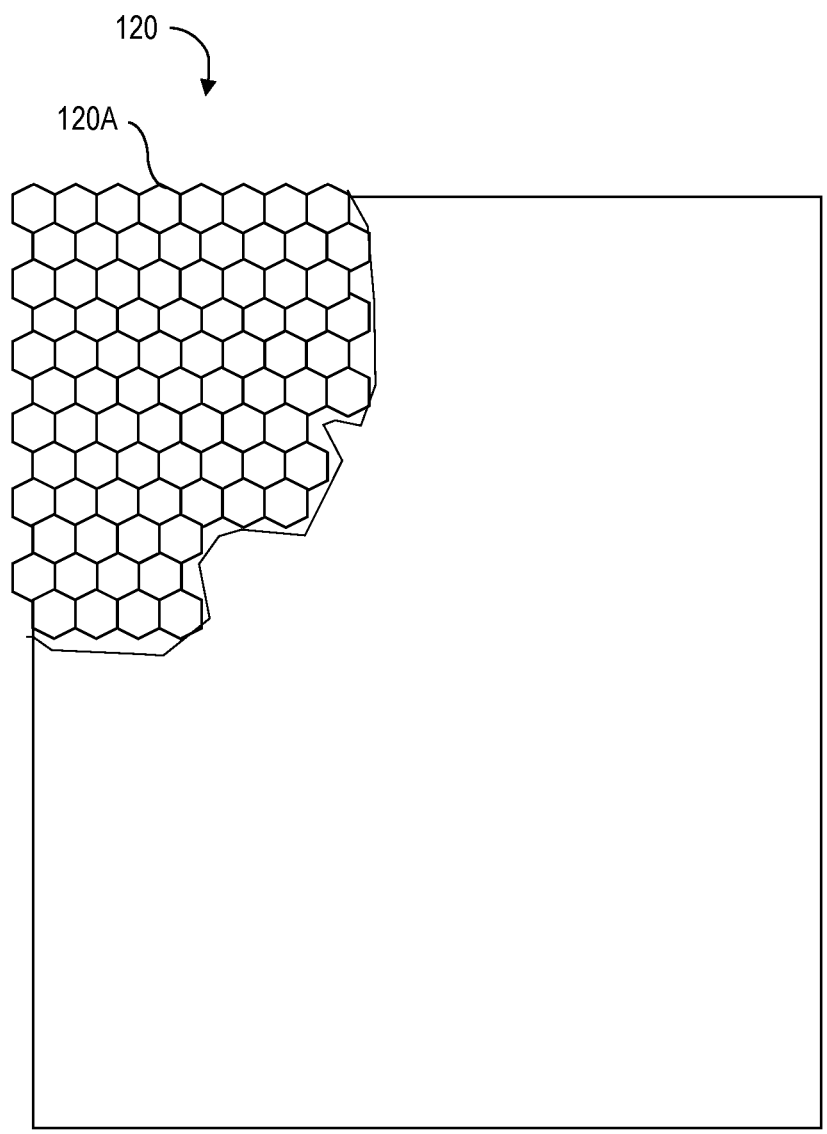
FIG. 1B is a diagram illustrating a first photocatalytic cell that is assembled with the housing of FIG. 1A to provide the photocatalytic system.
Figure 1C:
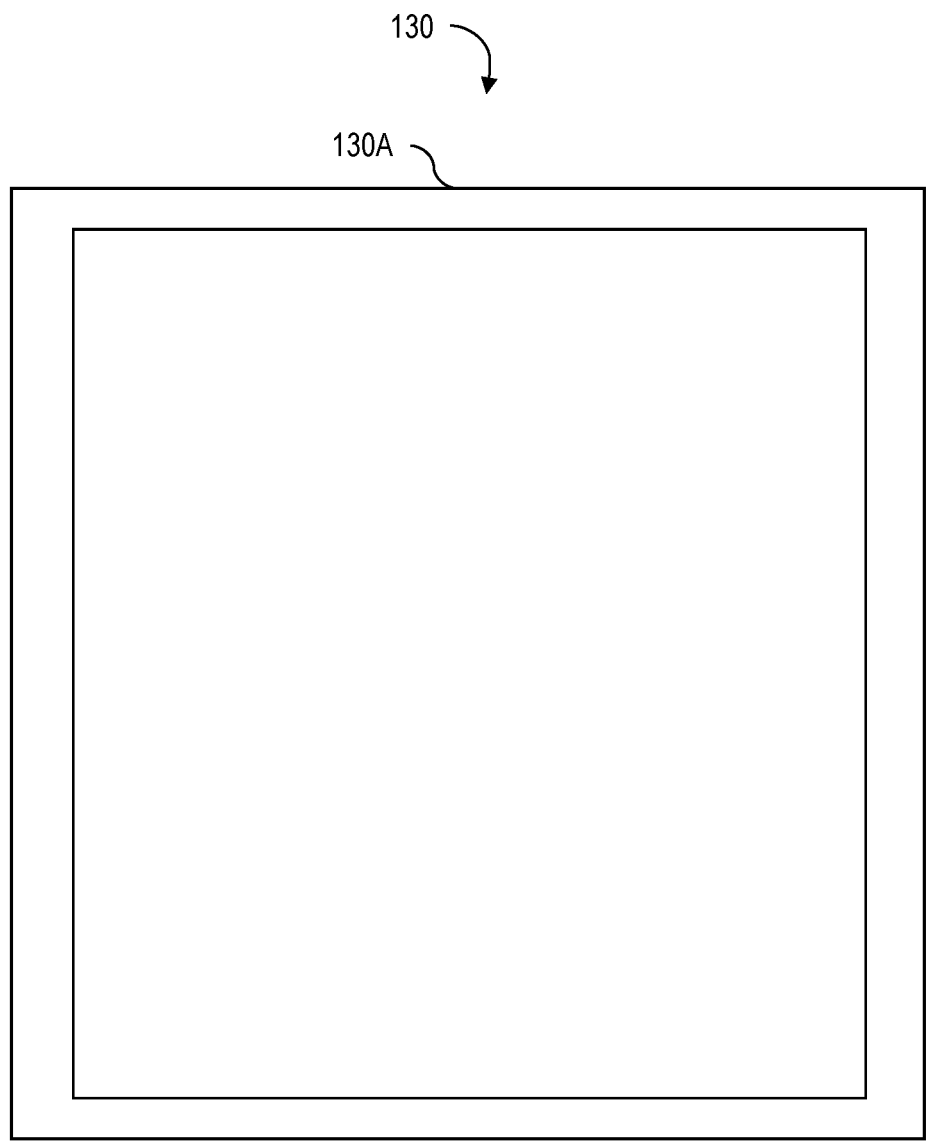
FIG. 1C is a diagram illustrating a unitary structure that is assembled with the housing of FIG. 1A, and the first photocatalytic cell of FIG. 1B to provide the photocatalytic system.
Figure 1D:
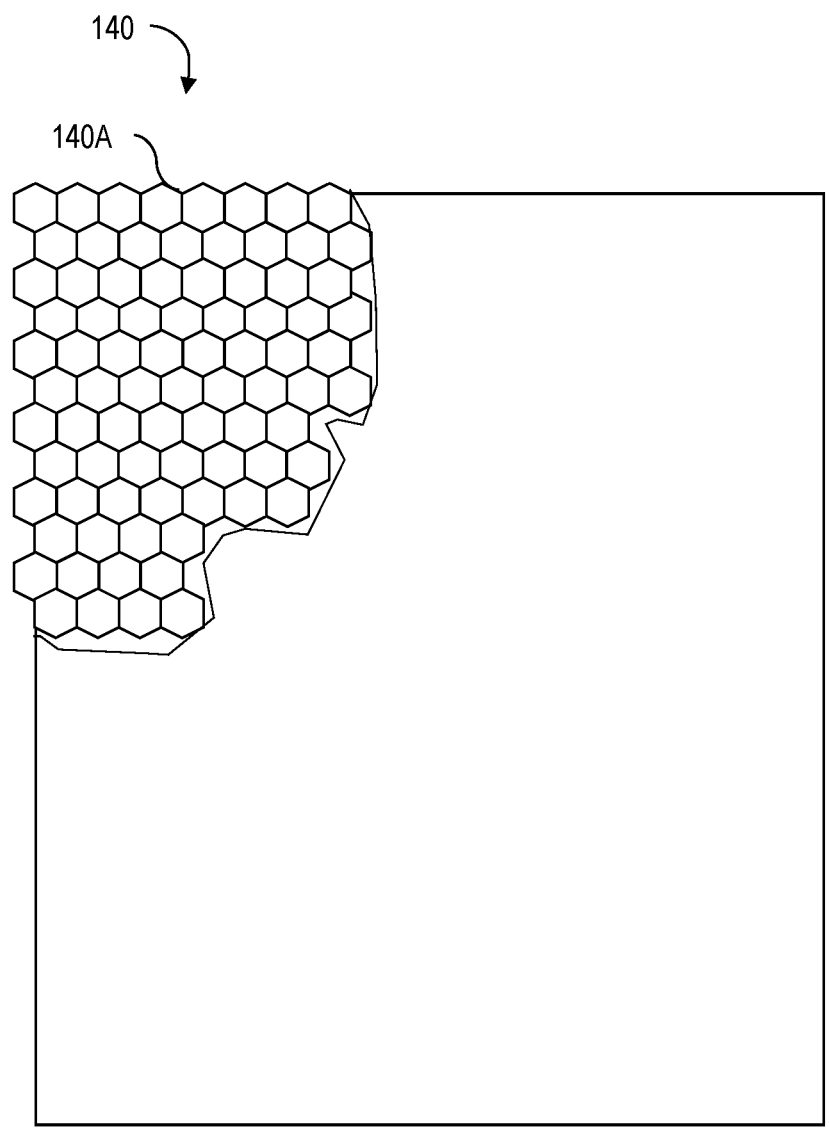
FIG. 1D is a diagram illustrating a second photocatalytic cell that is assembled with the housing of FIG. 1A, the first photocatalytic cell of FIG. 1B, and the unitary structure of FIG. 1C to provide the photocatalytic system.

Referring now to the drawings, and particularly to FIG. 1A-FIG. 1D generally, components of a photocatalytic system 100 are illustrated. The system 100 includes in general, a housing 110 (FIG. 1A), a first photocatalytic cell 120 (FIG. 1B), a unitary removable structure 130 (FIG. 1C), and a second photocatalytic cell 140 (FIG. 1D).

Referring now to FIG. 1A, the housing 110 can take on any desired shape, depending upon the specific application. However, as illustrated, the housing 110 includes a top 110A, a bottom 110B having an opening therethrough, a pair of opposing side surfaces 110C, 110D, a front side 110E and a back side 110F opposite the front side 110E. The front side 110E and the back side 110F are implemented in this illustrative embodiment, as a frame having an opening therethrough.

Referring now to FIG. 1B, the first photocatalytic cell 120 comprises shaped cell members 120A that define apertures that pass therethrough. For instance, in practical applications, the cell members 120A can comprise honeycombs. The honeycombs can be the same size or different sizes. Moreover, the shaped cell members 120A can be the same shape (e.g., honeycombs) or different shape configuration. Yet further, the shaped cell members 120A can be different sizes and shapes. Only a portion of the shaped cell members 120A are shown for convenience of illustration. However, in practice, the entirety of the photocatalytic cell 120 can comprise the shaped cell members 120A, or only a portion of the first photocatalytic cell can include shaped cell members 120A. Regardless, the shaped cell members 120A are photocatalytic, or are coated with a photocatalytic coating that reacts to UV energy. Moreover, the apertures through the shaped cell members 120A allow air to pass therethrough.

With reference to FIG. 1C, the unitary removable structure 130 includes a reflective surface and can have different shape configurations. For instance, the unitary removable structure 130 can be an elongate member having a cross-section that is circular, oval shaped, rectangular, rounded rectangular, triangular, or other shape. Moreover, the unitary removable structure 130 can have a variety of configurations, including open slots, holes, windows, etc., to as to allow air to pass entirely therethrough.

Turning to FIG. 1D, the second photocatalytic cell 140 comprises shaped cell members 140A that define apertures that pass therethrough. In a manner analogous to the shaped cell members 120A, the second photocatalytic cell 140 comprises shaped cell members 140A that define apertures that pass therethrough. For instance, in practical applications, the cell members 140A can comprise honeycombs. The honeycombs can be the same size or different sizes. Moreover, the shaped cell members 140A can be the same shape (e.g., honeycombs) or different shape configuration. Yet further, the shaped cell members 140A can be different sizes and shapes. Also, the shaped cell members 120A can be the same as, or different from the shaped cell members 140A. Only a portion of the shaped cell members 140A are shown for convenience of illustration. However, in practice, the entirety of the photocatalytic cell 140 can comprise the shaped cell members 140A, or only a portion of the first photocatalytic cell can include shaped cell members 140A. Regardless, the shaped cell members 140A are photocatalytic, or are coated with a photocatalytic coating that reacts to UV energy. Moreover, the apertures through the shaped cell members 140A allow air to pass therethrough.

With reference to FIG. 1A-1D generally, when assembled, the first photocatalytic cell 120 is inserted into the housing 110, e.g., adjacent to the front side 110E. For instance, the first photocatalytic cell 120 (when utilized) can be inserted through the open bottom 110B, e.g., into a guide that allows the first photocatalytic cell 120 to slide into position. Analogously, the second photocatalytic cell 140 (when utilized) is inserted into the housing 110, e.g., adjacent to the rear side 110F. For instance, the second photocatalytic cell 140 can be inserted through the open bottom 110B, e.g., into a guide that allows the second photocatalytic cell 140 to slide into position. The unitary removable structure 130 inserts into the housing 110 between the front side 110E and the rear side 110F.

Figure 2A:
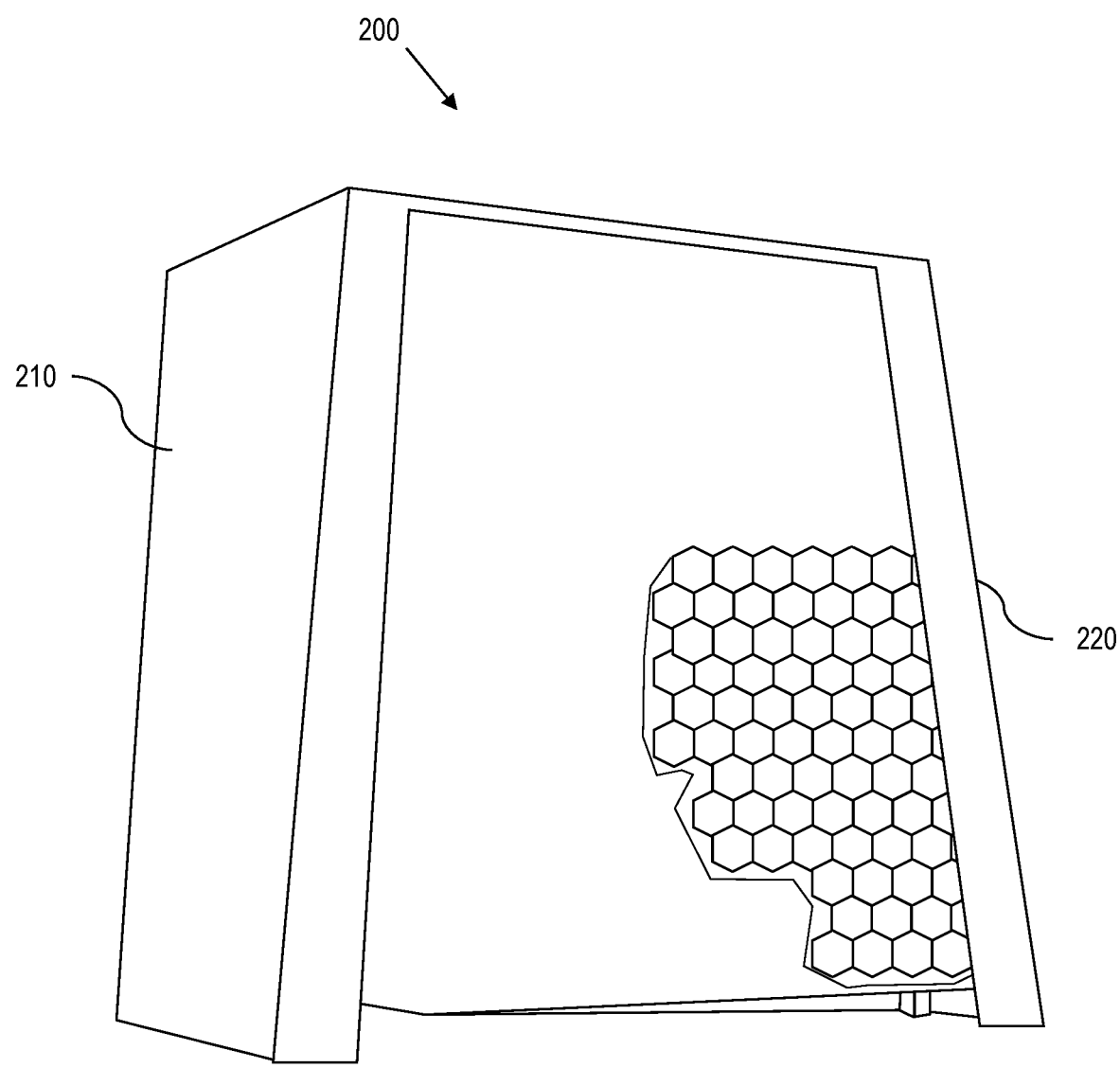
FIG. 2A is a diagram showing a front perspective view of a photocatalytic system for reducing airborne contaminants.
Figure 2B:
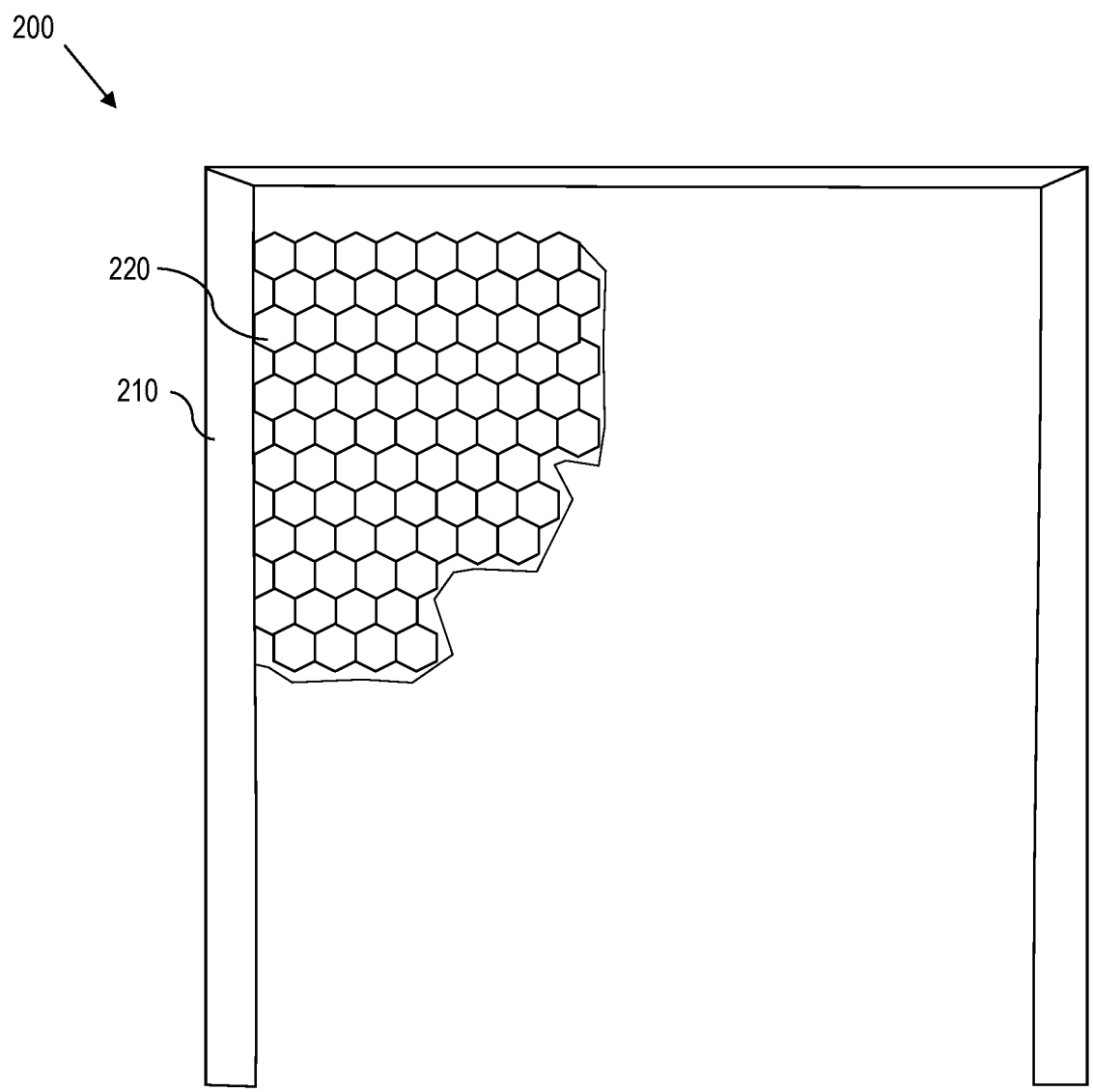
FIG. 2B is a diagram showing a front view of the system of FIG. 1A.
Figure 2C:
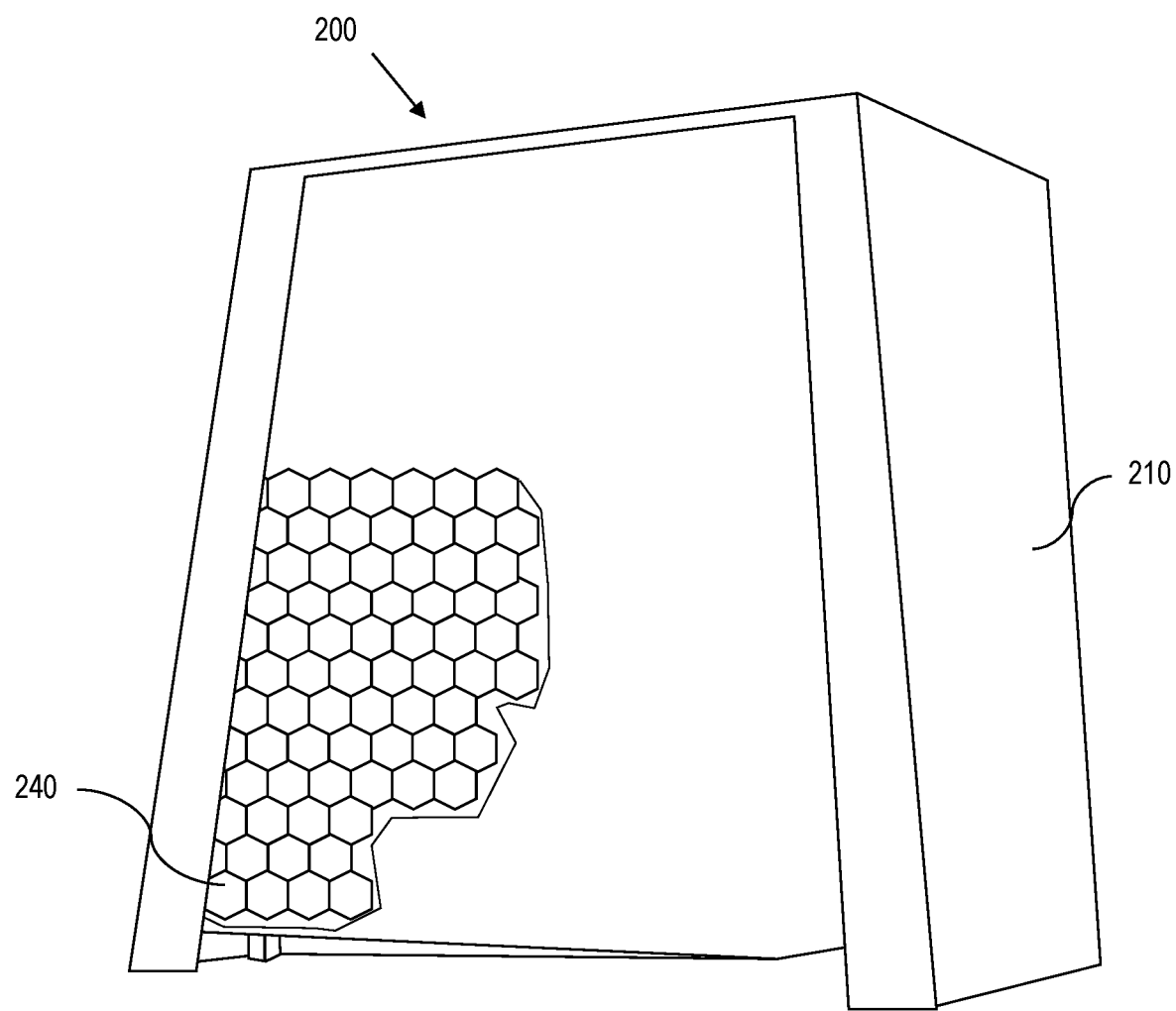
FIG. 2C is a diagram showing another front perspective view of the system of FIGS. 2A and 2B.
Figure 2D:
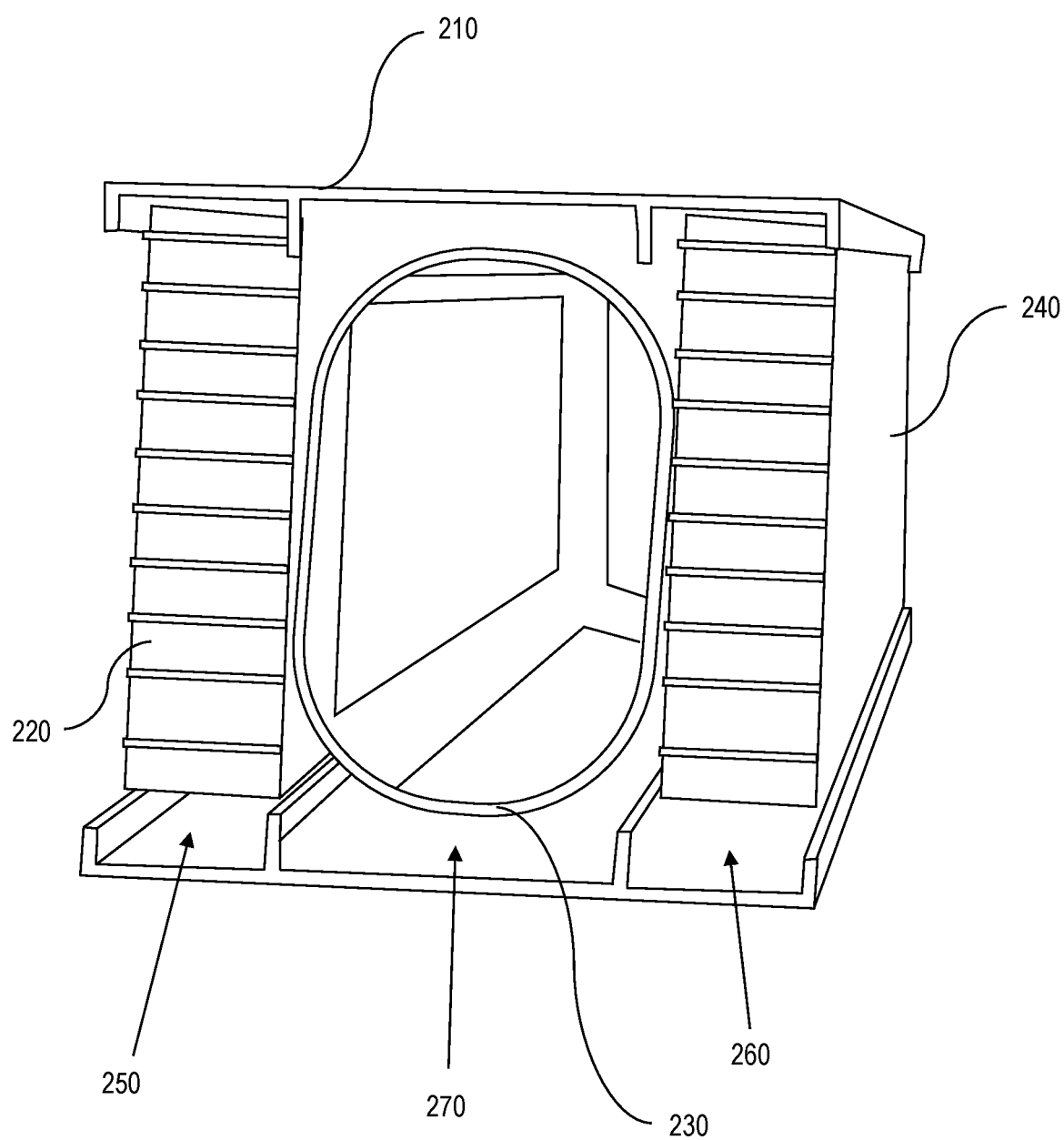
FIG. 2D is a diagram showing a bottom view of the system of FIGS. 2A through 2C.
Figure 2E:
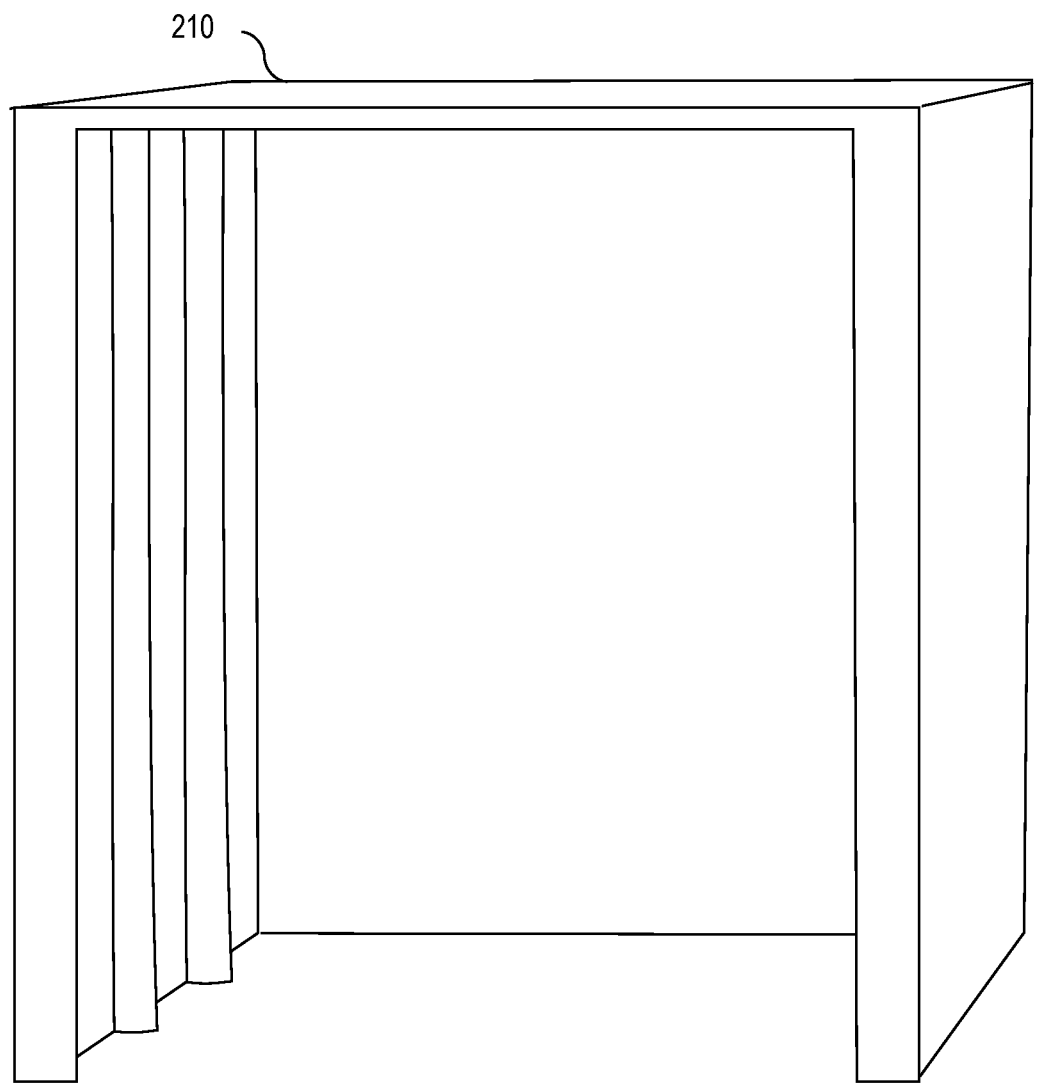
FIG. 2E is a diagram showing an a housing of the system of FIGS. 2A through 2D.
Figure 2F:
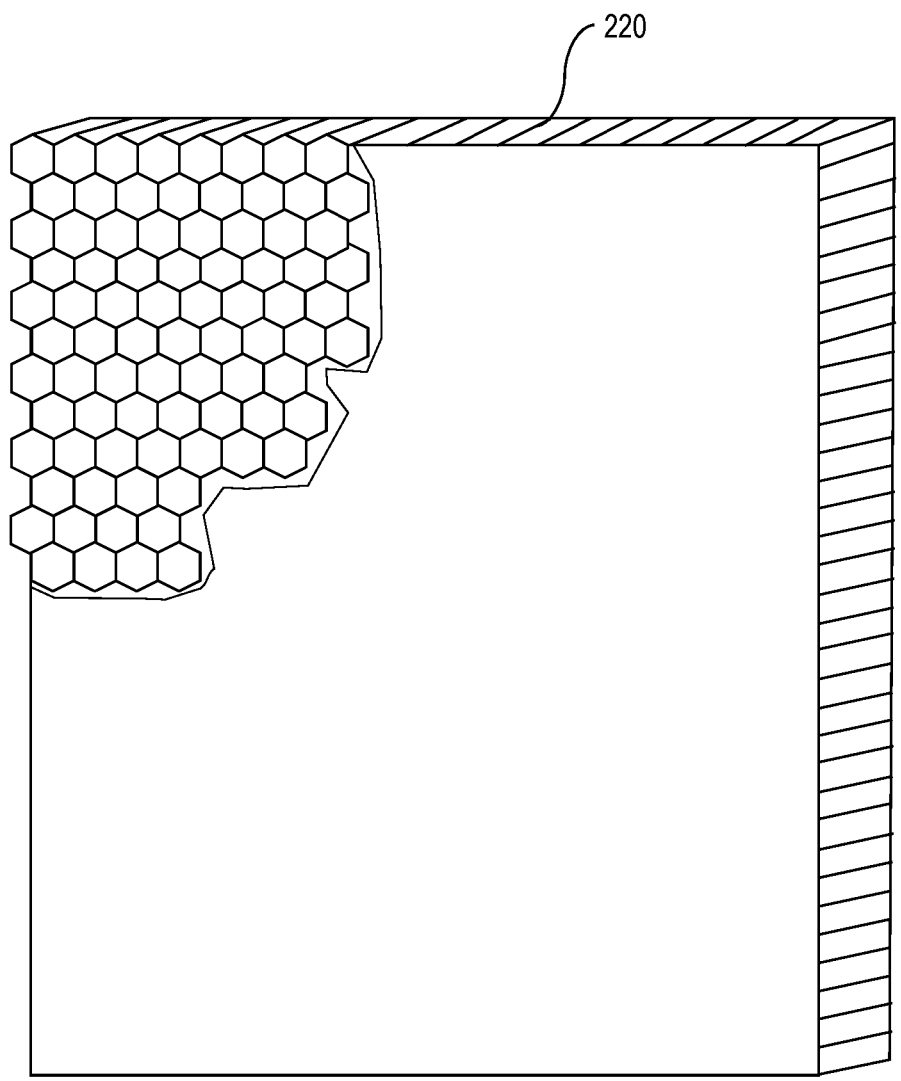
FIG. 2F is a diagram showing an example of a first photocatalytic cell for the system of FIGS. 2A through 2E.
Figure 2G:
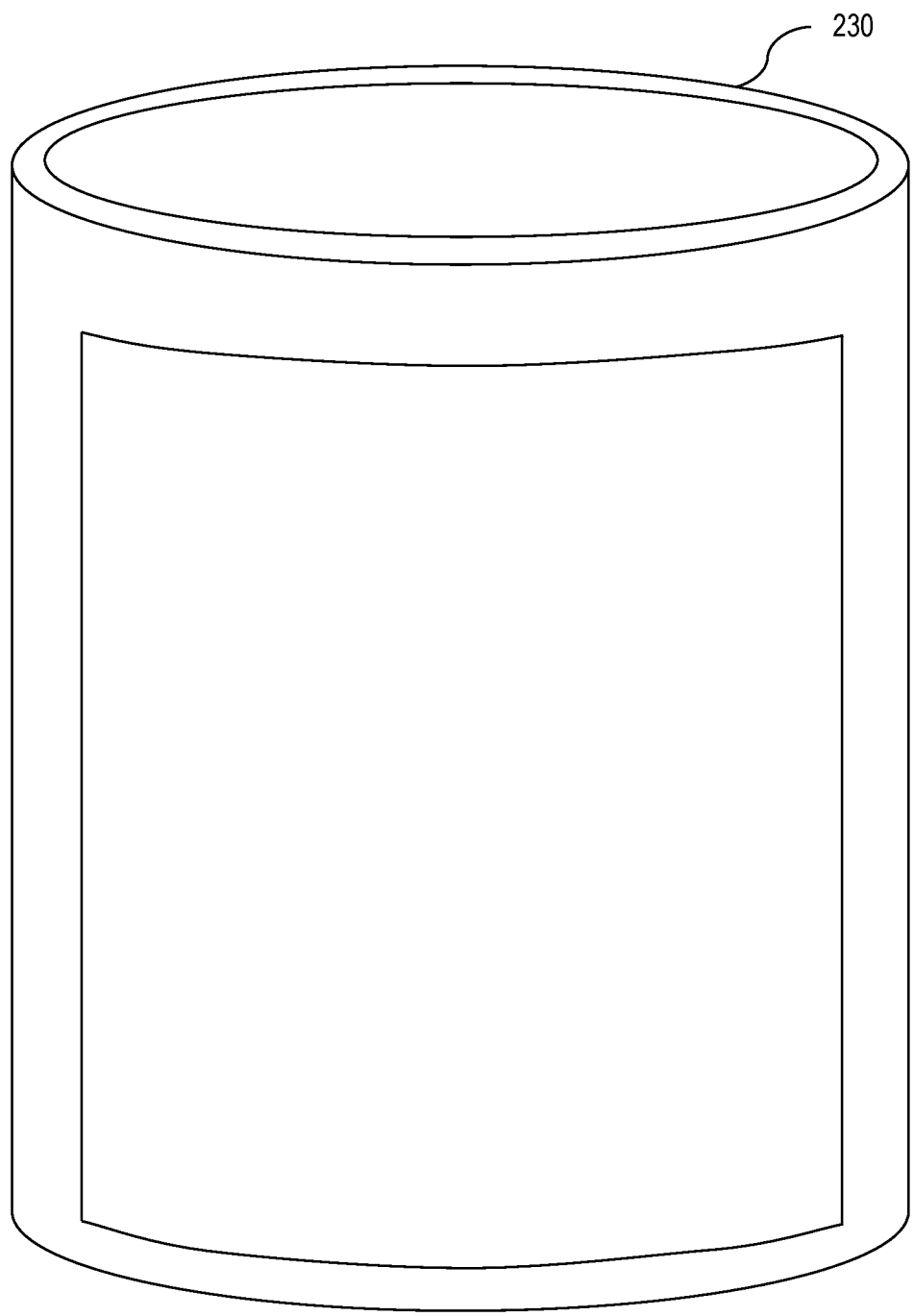
FIG. 2G is an example implementation of a removable unitary structure for the system of FIGS. 2A through 2F.
Figure 2H:
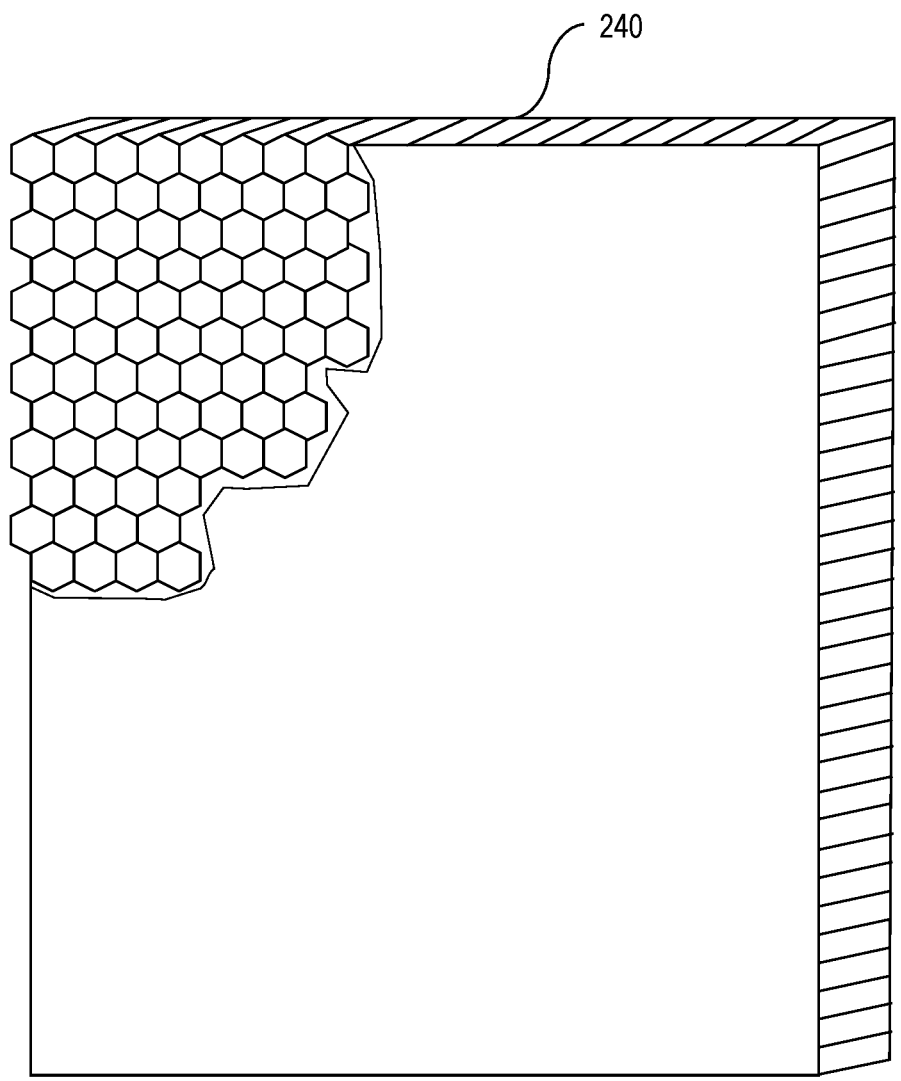
FIG. 2H is a diagram showing an example of a second photocatalytic cell for the system of FIGS. 2A through 2G.

Referring now to FIGS. 2A-2H, several views are illustrated of select components of a photocatalytic system 200 for reducing airborne contaminants. The system 200 is analogous to that described above with reference to FIG. 1. As such, like structure is illustrated with like reference numerals. Specifically, FIG. 2A shows a front perspective view of the system; FIG. 2B shows a front view; FIG. 2C shows a rear perspective view; FIG. 2D shows a bottom view; and FIG. 2E shows an perspective view of the housing; FIG. 2F shows a view of the first photocatalytic cell; FIG. 2G shows a view of the unitary removable structure 130; and FIG. 2H shows a view of the second photocatalytic cell.

As shown in FIGS. 2A through 2H (collectively designated as FIG. 2), the photocatalytic system 200 comprises a housing 210, a front photocatalytic cell 220, a unitary removable structure 230, and a back photocatalytic cell 240. In operation, air flows into the front photocatalytic cell 220, through the housing 210, and exists the housing 210 via the back photocatalytic cell 240. Although not shown in the figures, the system (when in operation) includes a UV emitter located so as to emit UV energy within the housing 210. For instance, an elongate UV bulb can be positioned between the two photocatalytic cells 220, 240, within a hollow defined by the unitary removable structure 230. The UV bulb can alternatively be located off to one side of the housing 210. Yet further, the UV bulb can be located in another structure that cooperates with the housing so as to direct light into the housing. Still further, the UV bulb can be in any other suitable location.

In the embodiment of FIG. 2A through FIG. 2H, the photocatalytic cells 220, 240 are shown as having a honeycomb matrix (or a hexagonal close-packed configuration). However, analogous to that described with reference to FIG. 1, other configurations are contemplated herein.

As best illustrated in FIG. 2D, the housing 210 comprises multiple slots. Each slot holds a respective one of the front photocatalytic cell 220, unitary removable structure 230, or back photocatalytic cell 240. For instance, because the housing 210 holds the front photocatalytic cell 220, the housing 210 comprises a front photocatalytic cell slot 250 that has a front slot height, a front slot width, and a front slot depth that corresponds to the height, width, and depth (respectively) of the front photocatalytic cell 220 (insofar as the front photocatalytic cell slot 250 must accommodate the front photocatalytic cell 220). At bottom, the front cell height corresponds to the front slot height, the front cell width corresponds to the front slot width, and the front cell depth corresponds to the front slot depth.

Similarly, because the housing 210 holds the back photocatalytic cell 240, the housing 210 comprises a back photocatalytic cell slot 260. In some embodiments, the back photocatalytic cell slot 260 has a back slot height, which can be substantially the same as, or different from, the front slot height. Similarly, the back photocatalytic cell slot 260 has a back slot width that can be substantially the same as, or different from, the front slot width. Finally, the back photocatalytic cell slot 260 has a back slot depth, which can be substantially the same as, or different from, the front slot depth. Similar to the front photocatalytic cell slot 250, the back photocatalytic cell slot 260 must accommodate the back photocatalytic cell 240. Again, the back cell height corresponds to the back slot height, the back cell width corresponds to the back slot width, and the back cell depth corresponds to the back slot depth.

Continuing with FIG. 2D, the housing 210 also accommodates the unitary removable structure 230. As such, the housing 210 comprises a reflector slot 270. The reflector slot 270 has a reflector slot height, which, for some embodiments, is substantially the same as the front slot height and, in other embodiments, is substantially different from the front slot height. The reflector slot 270 also has reflector slot width, which, for some embodiments, is again substantially the same as the front slot width and, in other embodiments, is substantially different from the front slot width. The reflector slot also has a reflector slot depth, which, for some embodiments, is again substantially the same as the front slot depth and, in other embodiments, is substantially different from the front slot depth.

Thus, the unitary removable structure 230 must fit into the reflector slot. At bottom, the dimensions of the reflector slot 270 are chosen to accommodate the dimensions of the unitary removable structure 230.

The unitary removable structure 230 provides a mechanism by which the UV energy is reflected, thereby increasing UV exposure of the photocatalytic cells 220, 240. Because the unitary removable structure 230 is both unitary (meaning, a single piece) and removable, the unitary removable structure 230 provides a more streamlined manufacturing process than, for example, the use of multiple reflectors.

An embodiment of a unitary removable structure 330 is shown in FIGS. 3A through 3D (collectively, FIG. 3). The unitary removable structure 330 is analogous to the unitary removable structure 130 (FIG. 1) and unitary removable structure 230 (FIG. 2A through FIG. 2H) unless otherwise noted. As such, the unitary removable structure 330 can be used with the system 100 (FIG. 1) and/or the system 200 (FIGS. 2A through 2H).

Figure 3A:
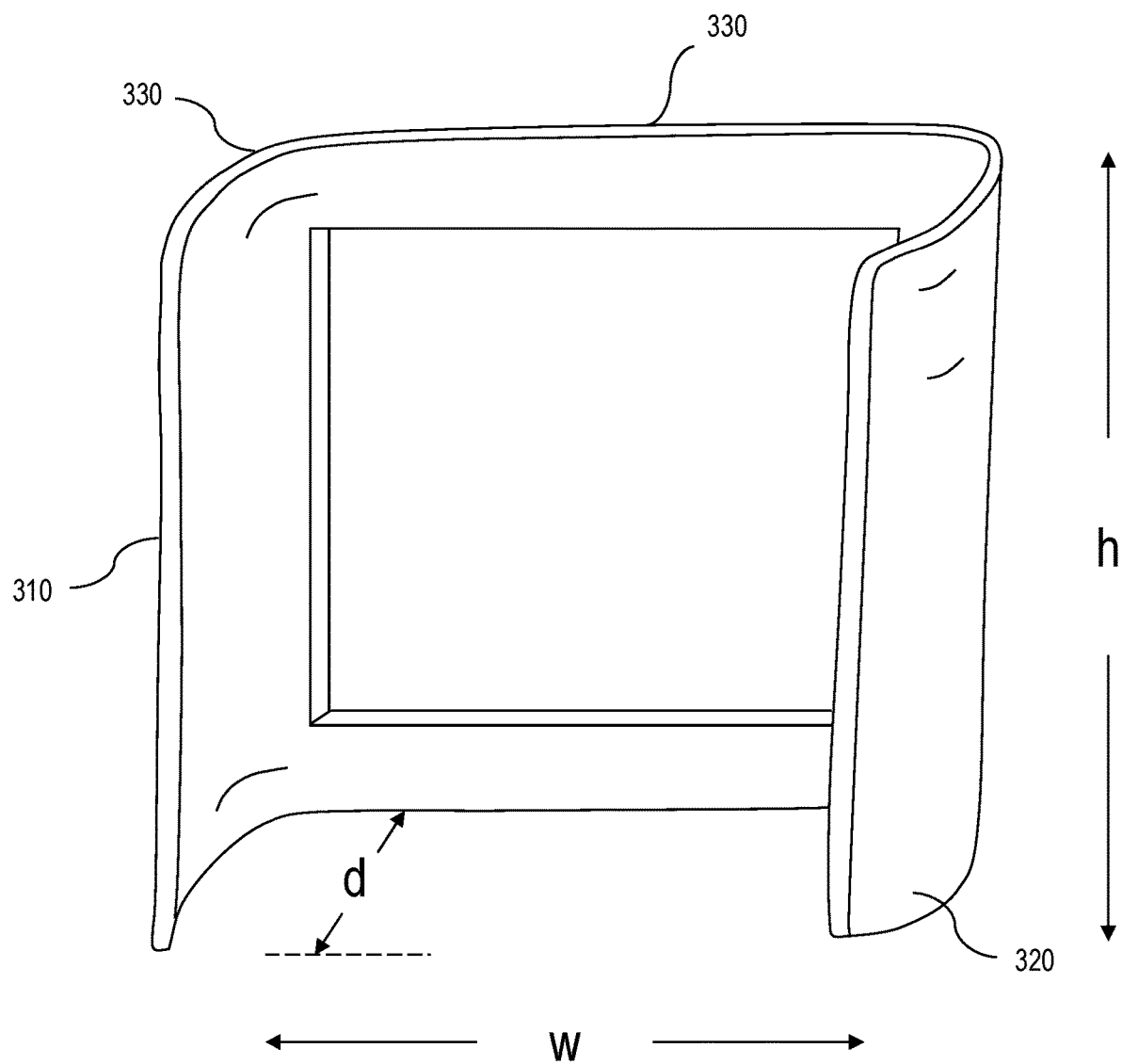
FIG. 3A is a diagram showing an example embodiment of a unitary removable structure.
Figure 3B:
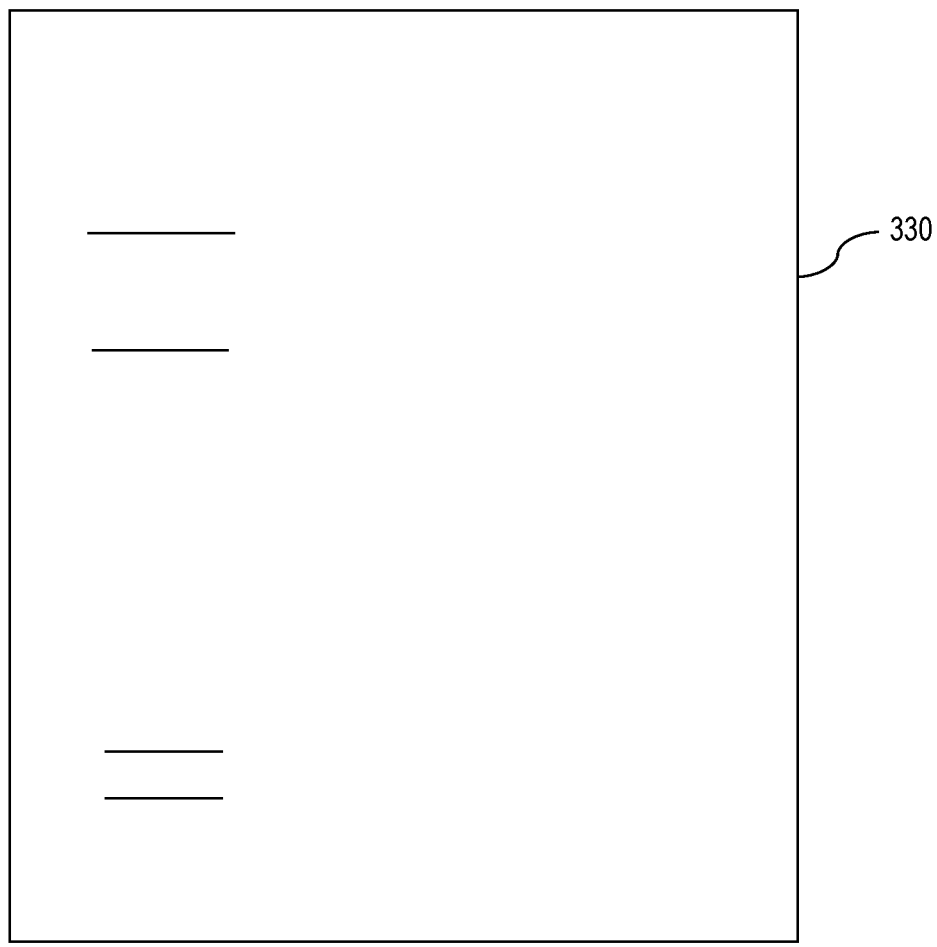
FIG. 3B is a diagram showing a side view of the unitary removable structure of FIG. 3A.
Figure 3C:
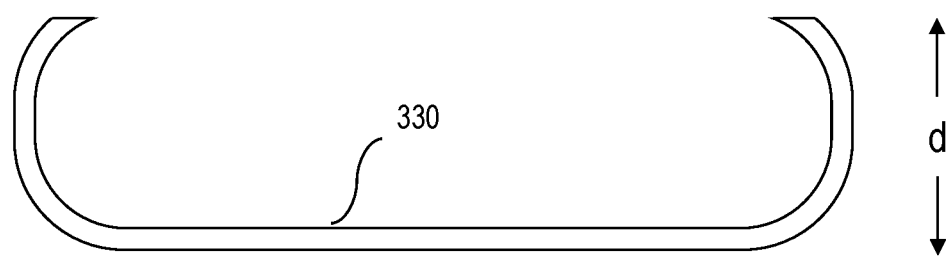
FIG. 3C is a diagram showing a top view of the unitary removable structure of FIG. 3A.
Figure 3D:
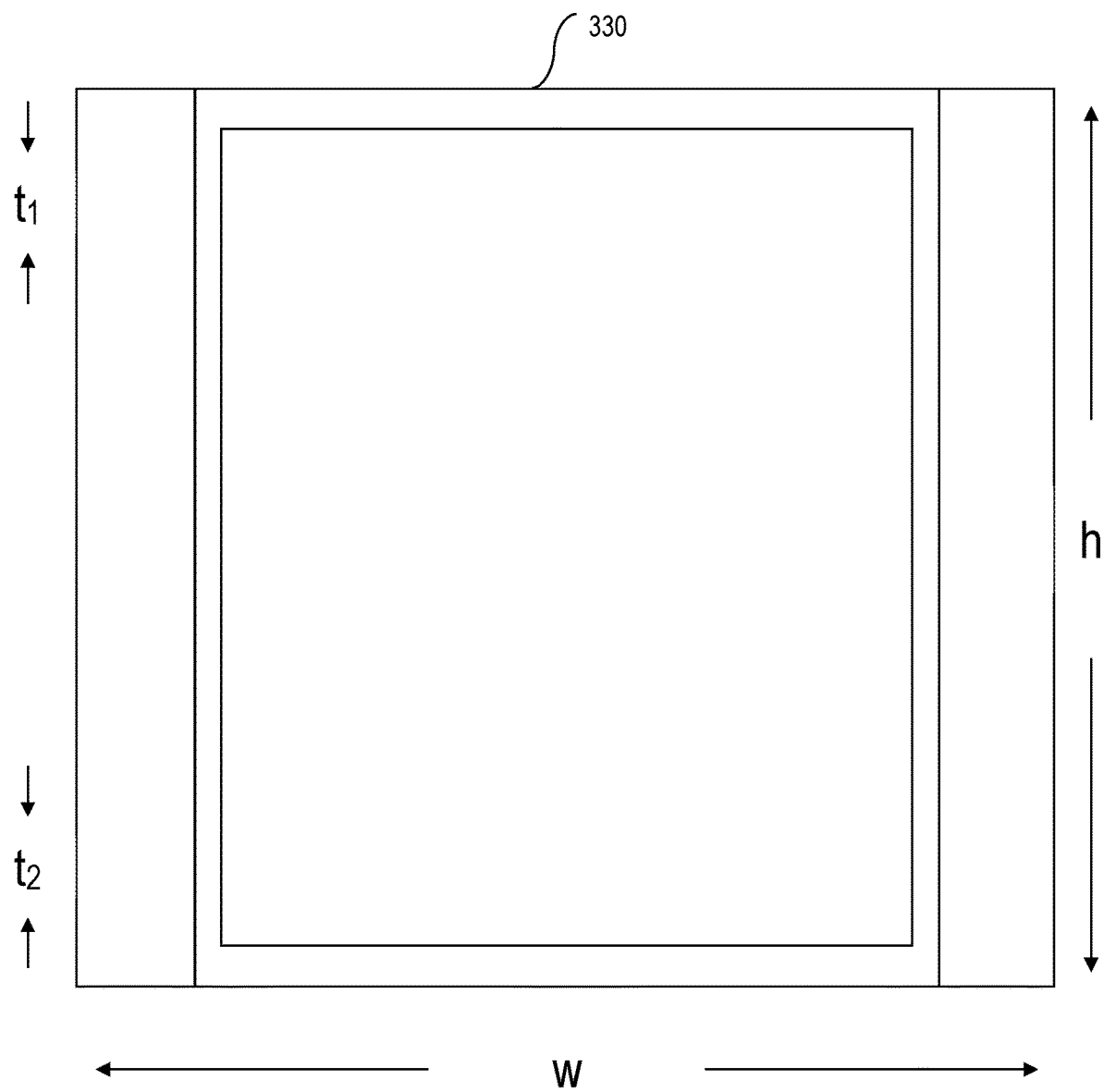
FIG. 3D is a diagram showing a front view of the unitary removable structure of FIG. 3A.

Specifically, FIG. 3A shows a perspective view of the unitary removable structure 330, which can be utilized with any of the systems 100, 200 described more fully herein. FIG. 3B shows a side view of the unitary removable structure 330; FIG. 3C shows a top view of the unitary removable structure 330; and FIG. 3D shows a front view of the unitary removable structure 330.

Referring to FIG. 3A through FIG. 3D generally, the unitary removable structure 330 comprises a first reflective portion 330A that is seamlessly integrated into the unitary removable structure 330. When the system is assembled and operating, the first reflective portion 330A receives UV light from a UV emitter and reflects the UV light to the photocatalytic cells (see photocatalytic cells 120, 140, FIG. 1; photocatalytic cells 220, 240, FIG. 2). The unitary removable structure 330 also comprises a second reflective portion 330B, which is also seamlessly integrated into the unitary removable structure 330. The second reflective portion 330B receives the UV light from the UV emitter and reflects the UV light to the photocatalytic cells (see photocatalytic cells 120, 140, FIG. 1; photocatalytic cells 220, 240, FIG. 2). As shown in FIG. 3, a connective structure 330B is seamlessly integrated into the unitary removable structure 330 and connects the first reflective portion 330A to the second reflective portion 330B. As noted above, the dimensions of the unitary removable structure 330 corresponds to the dimensions of the reflector slot, meaning that the height (h), width (w), and depth (d) of the unitary removable structure 330 corresponds to the reflector slot height, the reflector slot depth, and the reflector slot width, respectively.

By providing a unitary removable reflector 330, the disclosed embodiments permit greater exposure of UV energy to the photocatalytic cells (see photocatalytic cells 120, 140, FIG. 1; photocatalytic cells 220, 240, FIG. 2) and, concurrently, allow for more streamlined assembly of UV-based photocatalytic systems. In other words, unlike conventional systems that require multiple reflectors, the disclosed embodiments realize greater efficiency in both the manufacturing process as well as in the reduction of airborne contaminants.

Figure 4:
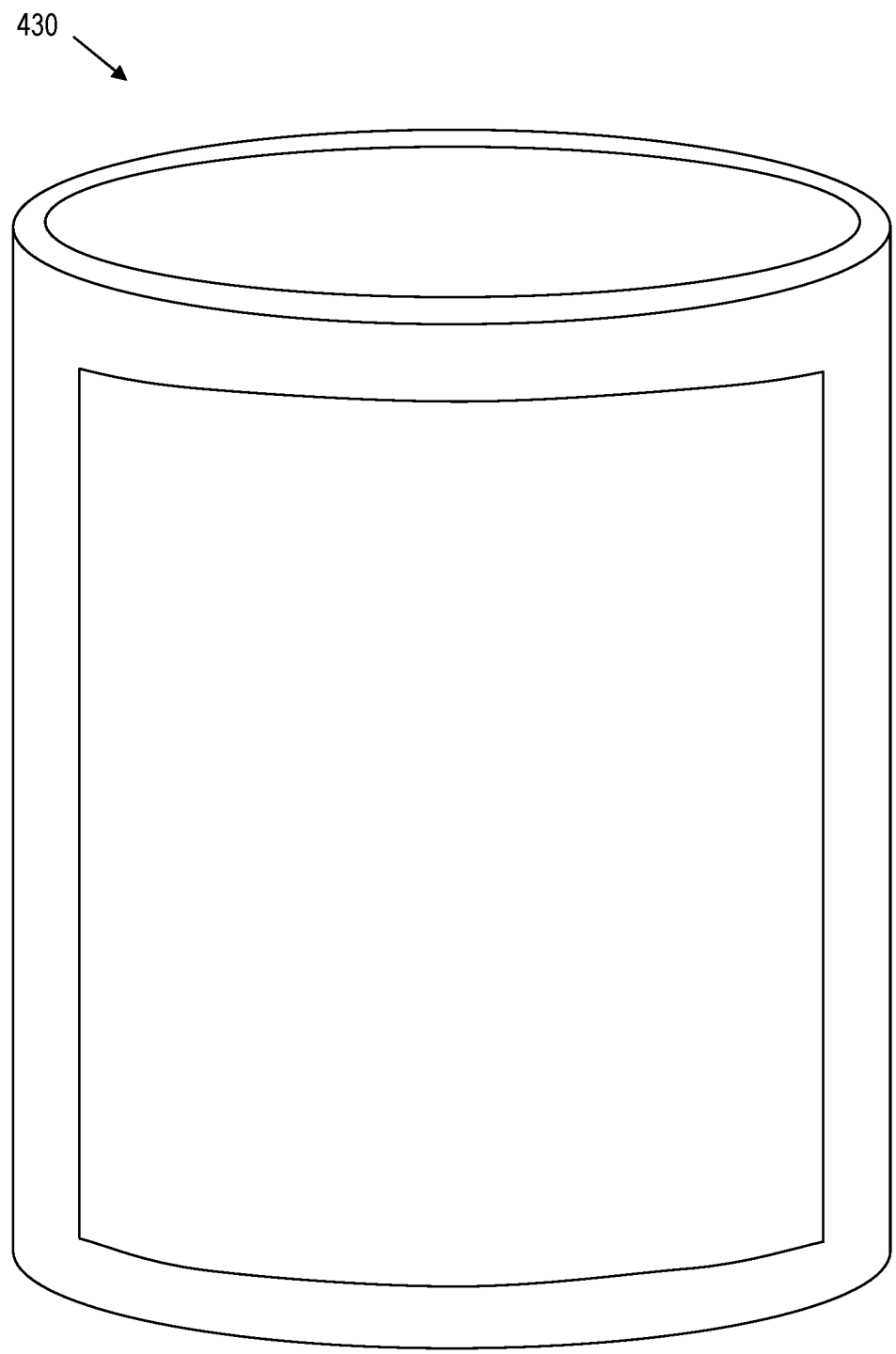
FIG. 4 is another example embodiment of a unitary removable structure.

FIG. 4 illustrates yet another example of a unitary removable structure, according to further aspects of the present disclosure. In the illustrated embodiment, the unitary removable structure forms a generally tubular structure, as compared to the curved structure of FIG. 3A through FIG. 3D. The illustrated unitary structure includes large windows to allow maximum airflow therethrough and provides reflective sides.

Figure 5:
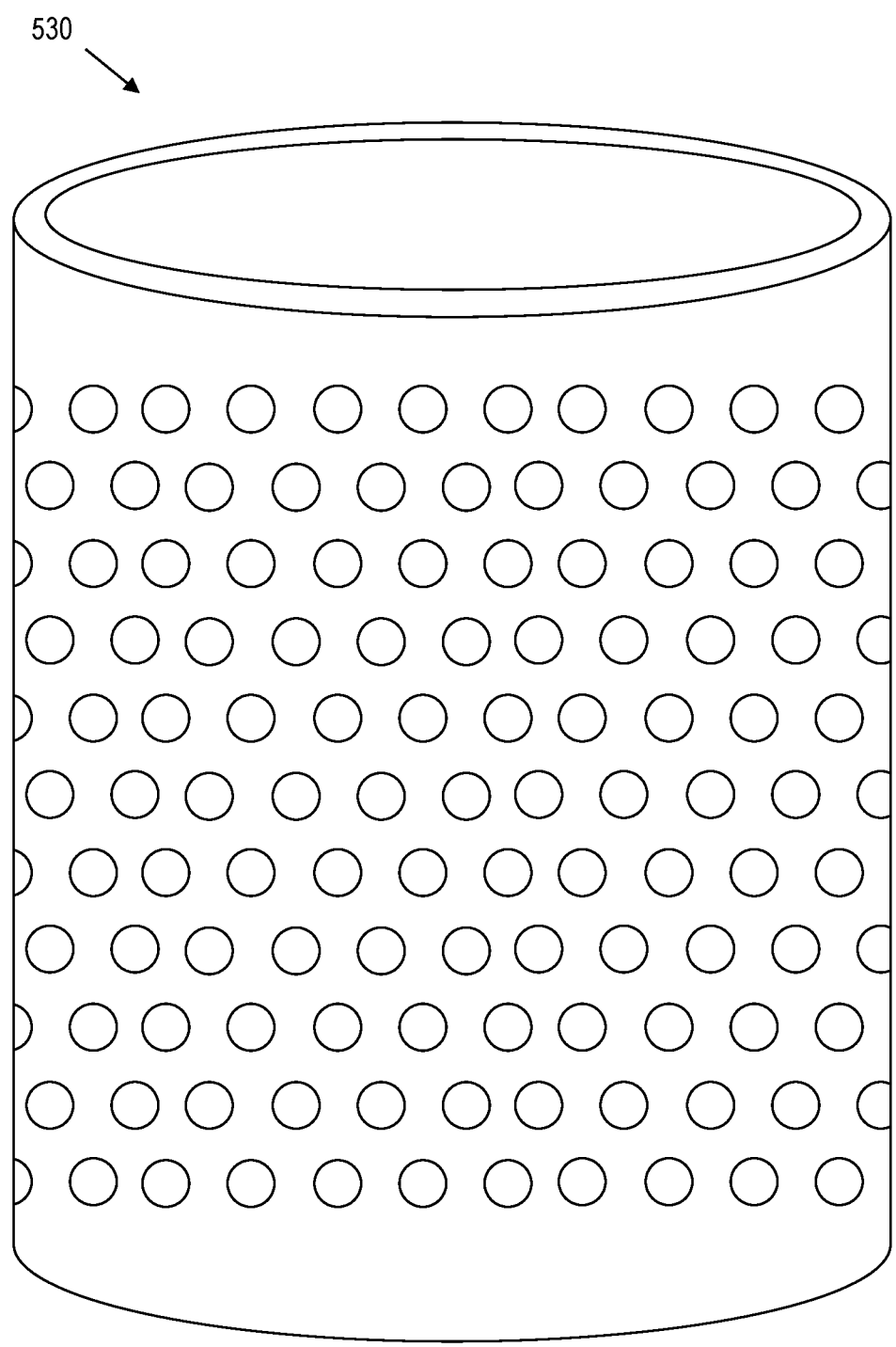
FIG. 5 is yet another example embodiment of a unitary removable structure.

FIG. 5 illustrates still another example of a unitary removable structure, according to further aspects of the present disclosure. In the illustrated embodiment, the unitary removable structure forms a generally tubular structure similar to that of FIG. 4. However, there are some differences compared to the structure of FIG. 4. For instance, instead of including large windows therethrough, the inside surface is reflective. Moreover, there are a plurality of apertures around at least two (2) regions to allow airflow therethrough. Thus, the embodiment of FIG. 4 provides relatively less reflective surface and more open area for airflow. By contrast, the embodiment of FIG. 5 provides relatively more reflective area with less aperture area for airflow.

In practice, the unitary removable structure can take on other appearances, shapes, etc. Regardless, any of the illustrated unitary removable structures can be installed in any of the disclosed systems (e.g., system 100, FIG. 1; system 200, FIG. 2, etc.), simply by sliding in a unitary removable structure having a desired configuration.

Any process descriptions or blocks in flow charts should be understood as being performed out of order from that shown or discussed, including substantially concurrently or in reverse order, depending on the functionality involved, as would be understood by those reasonably skilled in the art of the present disclosure.

Although exemplary embodiments have been shown and described, it will be clear to those of ordinary skill in the art that a number of changes, modifications, or alterations to the disclosure as described may be made. All such changes, modifications, and alterations should therefore be seen as within the scope of the disclosure.

What is claimed is:

1. A photocatalytic system for reducing airborne contaminants using an ultraviolet (UV) emitter and photocatalytic cells, the system comprising:
   a housing comprising:
      a front photocatalytic cell slot comprising:
         a front slot height;
         a front slot width; and
         a front slot depth;
      a reflector slot comprising:
         a reflector slot height that is substantially the same as the front slot height;
         a reflector slot width that is substantially the same as the front slot width; and
         a reflector slot depth;
      a back photocatalytic cell slot comprising:
         a back slot height that is substantially the same as the front slot height;
         a back slot width that is substantially the same as the front slot width; and
         a back slot depth;
   a front photocatalytic cell located in the front photocatalytic cell slot, the front photocatalytic cell comprising:
      a front cell height that corresponds to the front slot height;
      a front cell width that corresponds to the front slot width; and
      a front cell depth that corresponds to the front slot depth;
   a unitary removable curved structure located in the reflector slot, the unitary removable curved structure being a tubular structure, the unitary removable curved structure comprising:
      a first reflective portion comprising:
         a first portion height that corresponds to the reflector slot height; and
         a first portion width that corresponds to the reflector slot depth;
      a second reflective portion comprising:
         a second portion height corresponds to the reflector slot height; and
         a second portion width that corresponds to the reflector slot depth;
      a first connective structure that connects the first reflective portion with the second reflective portion to form a first window in the unitary removable curved structure, the first connective structure separating the first reflective portion from the second reflective portion by a distance that corresponds approximately to the reflector slot width;
      a second connective structure that connects the first reflective portion with the second reflective portion to form a second window in the unitary removable curved structure, the second connective structure separating the first reflective portion from the second reflective portion by a distance that corresponds approximately to the reflector slot width; and
   a back photocatalytic cell located in the back photocatalytic cell slot, the back photocatalytic cell comprising:
      a back cell height that corresponds to the back slot height;
      a back cell width that corresponds to the back slot width; and
      a back cell depth that corresponds to the back slot depth.

2. A photocatalytic system for reducing airborne contaminants using an ultraviolet (UV) emitter and photocatalytic cells, the system comprising:
   a housing comprising a front portion having an opening therethrough, and a back portion opposite the front portion, the back portion also having an opening therethrough;
   a front photocatalytic cell located in the housing adjacent to the front portion;
   a back photocatalytic cell located in the housing adjacent to the back portion; and
   a unitary removable curved structure slidably positionable within the housing between the front photocatalytic cell and the back photocatalytic cell, the unitary removable curved structure being a tubular structure comprising:
      reflective sides; and
      windows located between the reflective sides for airflow.

3. The system of claim 2, wherein:
   the front photocatalytic cell comprises a first honeycomb matrix; and
   the back photocatalytic cell comprises a second honeycomb matrix.

4. The system of claim 2, wherein the housing comprises a front photocatalytic cell slot for securing therewithin the front photocatalytic cell, the front photocatalytic cell slot comprising:
   a front slot height;
   a front slot width; and
   a front slot depth.

5. The system of claim 4, wherein the front photocatalytic cell comprises:
   a front cell height that corresponds to the front slot height;
   a front cell width that corresponds to the front slot width; and
   a front cell depth that corresponds to the front slot depth.

6. The system of claim 4, wherein the housing further comprises a back photocatalytic cell slot for securing therewithin the back photocatalytic cell, the back photocatalytic cell slot comprising:
   a back slot height that is substantially the same as the front slot height;
   a back slot width that is substantially the same as the front slot width; and
   a back slot depth.

7. The system of claim 6, wherein the back photocatalytic cell comprises:
   a back cell height that corresponds to the back slot height;
   a back cell width that corresponds to the back slot width; and
   a back cell depth that corresponds to the back slot depth.

8. The system of claim 2, wherein the unitary removable curved structure comprises:
a first reflective portion;
a second reflective portion;
a first connective structure that connects the first reflective portion with the second reflective portion to form a first window in the unitary removable curved structure; and
a second connective structure that connects the first reflective portion with the second reflective portion to form a second windows in the unitary removable curved structure.

9. The system of claim 8, wherein the housing comprises a reflector slot comprising:
a reflector slot height;
a reflector slot width; and
a reflector slot depth.

10. The system of claim 9, wherein:
the first reflective portion comprises:
a first portion height that corresponds to the reflector slot height; and
a first portion width that corresponds to the reflector slot depth;
the second reflective portion comprises:
a second portion height that corresponds to the reflector slot height; and
a second portion width that corresponds to the reflector slot depth; and
the connective structure separates the first reflective portion from the second reflective portion by a distance that corresponds approximately to the reflector slot width.

11. A photocatalytic system for reducing airborne contaminants using an ultraviolet (UV) emitter and photocatalytic cells, the system comprising:
a unitary removable curved structure being tubular in structure;
a first reflective portion that is seamlessly integrated into the unitary removable curved structure, the first reflective portion for receiving UV light from the UV emitter and reflecting the UV light to the photocatalytic cells;
a second reflective portion that is seamlessly integrated into the unitary removable curved structure, the second reflective portion for receiving the UV light from the UV emitter and reflecting the UV light to the photocatalytic cells;
a first connective structure that is seamlessly integrated into the unitary removable curved structure, the first connective structure mechanically connecting the first reflective portion with the second reflective portion, the first connective structure separating the first reflective portion from the second reflective portion by a distance that is large enough for the UV emitter to be located between the first reflective portion and the second reflective portion, the first connective structure providing a first window between the first reflective portion and the second reflective portion; and
a second connective structure that is seamlessly integrated into the unitary removable curved structure, the second connective structure mechanically connecting the first reflective portion with the second reflective portion, the second connective structure separating the first reflective portion from the second reflective portion by a distance that is large enough for the UV emitter to be located between the first reflective portion and the second reflective portion, the second connective structure providing a second window between the first reflective portion and the second reflective portion.

12. The photocatalytic system of claim 11, further comprising:
a housing comprising:
a front portion having a first opening therethrough, the first opening being substantially perpendicular to the first reflective portion, the first opening further being substantially perpendicular to the second reflective portion; and
a back portion opposite the front portion, the back portion having a second opening therethrough, the second opening being substantially perpendicular to the first reflective portion, the second opening further being substantially perpendicular to the second reflective portion.

13. The photocatalytic system of claim 12, further comprising:
a front photocatalytic cell located near the front portion; and
a back photocatalytic cell located near the back portion.

14. The photocatalytic system of claim 13, wherein the front photocatalytic cell comprises a honeycomb structure.

15. The photocatalytic system of claim 13, wherein the second photocatalytic cell comprises a honeycomb structure.

16. The photocatalytic system of claim 12, wherein the housing further comprises:
a front photocatalytic cell slot for securing therewithin a front photocatalytic cell, the front photocatalytic cell slot comprising:
a front slot height;
a front slot width; and
a front slot depth;
a reflector slot for securing therewithin the unitary removable curved structure, the reflector slot comprising:
a reflector slot height that is substantially the same as the front slot height;
a reflector slot width that is substantially the same as the front slot width; and
a reflector slot depth;
a back photocatalytic cell slot for securing therewithin a back photocatalytic cell, the back photocatalytic cell slot comprising:
a back slot height that is substantially the same as the front slot height;
a back slot width that is substantially the same as the front slot width; and
a back slot depth.

17. The photocatalytic system of claim 16, wherein the first connective structure comprises a connective structure length that is less than the reflector slot depth.

18. The photocatalytic system of claim 17, wherein the UV emitter is located between the first reflective portion, the second reflective portion, the front photocatalytic cell slot, and the back photocatalytic cell slot.

* * * * *